(12) United States Patent
Honda et al.

(10) Patent No.: US 8,421,031 B2
(45) Date of Patent: Apr. 16, 2013

(54) PARTICLE BEAM THERAPY SYSTEM

(75) Inventors: Taizo Honda, Tokyo (JP); Masahiro Ikeda, Tokyo (JP); Yuehu Pu, Tokyo (JP); Kazushi Hanakawa, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 63 days.

(21) Appl. No.: 13/258,772

(22) PCT Filed: Mar. 10, 2011

(86) PCT No.: PCT/JP2011/055639
§ 371 (c)(1),
(2), (4) Date: Sep. 22, 2011

(87) PCT Pub. No.: WO2012/120678
PCT Pub. Date: Sep. 13, 2012

(65) Prior Publication Data
US 2012/0228521 A1 Sep. 13, 2012

(51) Int. Cl.
*H01J 3/26* (2006.01)
*A61N 5/10* (2006.01)

(52) U.S. Cl.
USPC .................. 250/398; 250/396 R; 250/492.3

(58) Field of Classification Search ....... 250/396 R–396 ML, 492.1, 492.3
See application file for complete search history.

(56) References Cited

U.S. PATENT DOCUMENTS

| | | | |
|---|---|---|---|
| 7,772,577 B2 | 8/2010 | Saito et al. | |
| 2006/0102856 A1* | 5/2006 | Matsuda et al. | 250/492.22 |
| 2009/0065706 A1* | 3/2009 | Saito et al. | 250/396 ML |
| 2009/0184263 A1* | 7/2009 | Moriyama et al. | 250/492.3 |

FOREIGN PATENT DOCUMENTS

| | | | |
|---|---|---|---|
| JP | 10-155922 A | | 6/1998 |
| JP | 10155922 A | * | 6/1998 |
| JP | 10-277170 A | | 10/1998 |

(Continued)

OTHER PUBLICATIONS

International Search Report (PCT/ISA/210) issued on May 24, 2011, by Japanese Patent Office as the International Searching Authority for International Application No. PCT/JP2011/055639 (in Japanese).

(Continued)

*Primary Examiner* — Jack Berman
*Assistant Examiner* — David E Smith
(74) *Attorney, Agent, or Firm* — Buchanan Ingersoll & Rooney PC (57) ABSTRACT

The objective is to obtain a particle beam therapy system that can suppress the effect of a leakage dose. There are provided a scanning nozzle that irradiates in a predetermined direction a particle beam emitted from an accelerator; an irradiation control unit that controls operation of the irradiation nozzle in such a way that the particle beam of a predetermined dose is sequentially irradiated onto each of a plurality of spots set in a planar direction in an irradiation subject; and a control unit that on/off-controls emission of the particle beam from the accelerator. The irradiation control unit makes the irradiation nozzle scan in a diluting manner the particle beam onto a predetermined area in the irradiation subject, in a predetermined period after a time point when emission is switched from ON to OFF, or in a period from the time point when emission is switched from ON to OFF to a time point when the particle beam is cut off.

19 Claims, 6 Drawing Sheets

FOREIGN PATENT DOCUMENTS

| | | |
|---|---|---|
| JP | 2006-145213 A | 6/2006 |
| JP | 2007-311125 A | 11/2007 |
| JP | 2008-136523 A | 6/2008 |
| JP | 2009-045170 A | 3/2009 |
| JP | 2009-066106 A | 4/2009 |
| JP | 2011-000378 A | 1/2011 |

OTHER PUBLICATIONS

Written Opinion (PCT/ISA/237) issued on May 24, 2011, by Japanese Patent Office as the International Searching Authority for International Application No. PCT/JP2011/055639 (partial English translation).

* cited by examiner

PARTICLE BEAM THERAPY SYSTEM

TECHNICAL FIELD

The present invention relates to a particle beam therapy system utilizing a charged particle beam and particularly to a particle beam therapy system utilizing a scanning irradiation method.

BACKGROUND ART

In the particle beam therapy, therapy is implemented by irradiating a charged particle beam (particle beam) onto a diseased site, which is a therapy subject, so as to kill the tissues of the diseased site; in order to deliver a sufficient dose to the tissues of the diseased site without causing damage to the peripheral tissues thereof, there is required a particle beam therapy system that can appropriately control an irradiation dose and irradiation volume. In a particle beam therapy system utilizing a scanning irradiation method among methods of forming the irradiation volume, by scanning a charged particle beam supplied from an accelerator while positioning it by means of a scanning electromagnet and the like, there is performed irradiation of a predetermined dose for each small irradiation area (spot) so that an irradiation field is formed stepwise. In the case of, among scanning irradiation methods, the raster-scanning irradiation method and an irradiation method in which the raster-scanning irradiation method and the spot-scanning irradiation method are combined so that beam cutoff between spots is eliminated, a charged particle beam is irradiated without being cut off until irradiation onto a single slice is completed.

In contrast, in the case where the irradiation subject is an organ that moves with respiration, it is required to implement or interrupt the irradiation of a charged particle beam in synchronization with the respiratory phase so that irradiation can be performed only in a respiration state where the organ moves little and the position of the organ can readily be located. Also in the case where beam cutoff operation is performed at a completion time, of irradiation onto a last spot, that is a last time point for scanning irradiation onto each slice, it is required to cut off a beam. However, it is difficult to instantaneously cut off a charge particle beam emitted from an accelerator; therefore, a very small quantity of dose, which is referred to as a leakage dose, is irradiated in a period (although short) after the cutoff operation is started. Accordingly, a leakage dose is unnecessarily delivered to the spot where the cutoff operation is performed; therefore, there has been a problem that it is difficult to implement appropriate dose delivery conforming to a treatment plan. Thus, there has been proposed a particle beam therapy system (e.g., refer to Patent Document 1) in which in the transport path that connects an accelerator and an irradiation apparatus, there are provided a deflection electromagnet for changing a beam orbit and a beam dump for dumping a charged particle beam whose orbit has been changed so that the time required for cutting off a beam is shortened and hence a leakage dose is suppressed.

PRIOR ART REFERENCE

Patent Document

[Patent Document 1] Japanese Patent Application Laid-Open No. 2009-45170 (Paragraphs 0020 through 0029, FIG. 1)

DISCLOSURE OF THE INVENTION

Problems to be Solved by the Invention

However, even in the case of the foregoing particle beam therapy system, a time delay is caused because an orbit is changed; thus, it is difficult to securely eliminate a leakage dose. Furthermore, there has been a problem that the system becomes complex because, for example, for the purpose of cutting off a beam, additional devices such as a deflection electromagnet and a beam dump are required and for the purpose of disposing of neutrons produced in the beam dump, a transport path is modified.

The present invention has been implemented in order to solve the foregoing problems; the objective thereof is to obtain a particle beam therapy system that can suppress the effect of a leakage dose.

Means for Solving the Problems

A particle beam therapy system according to the present invention is provided with an accelerator that accelerates and emits a particle beam; two electromagnets whose scanning directions are different from each other; a scanning nozzle that irradiates in a predetermined direction a particle beam emitted from the accelerator; an irradiation control unit that controls operation of the irradiation nozzle in such a way that a particle beam of a predetermined dose is sequentially irradiated onto each of a plurality of spots set in a planar direction in an irradiation subject; and a control unit that on/off-controls emission of a particle beam from the accelerator. The particle beam therapy system is characterized in that the irradiation control unit makes the irradiation nozzle perform scanning for diluting a leakage dose (referred to as diluting scanning, hereinafter) on a predetermined area set in the planar direction in the irradiation subject, in a predetermined period after a time point when emission of the particle beam is switched from ON to OFF, or in a period from the time point when emission of the particle beam is switched from ON to OFF to a time point when the particle beam is cut off.

Advantage of the Invention

In a particle beam therapy system according to the present invention, even when a beam cutoff occurs while irradiation onto a predetermined spot is performed, a leakage dose arising during the beam cutoff is dispersed within a predetermined area in an irradiation subject; therefore, no unnecessary doses converge at a specific spot, so that a dose delivery that is closer to a treatment plan can be made.

BEST MODE FOR CARRYING OUT THE INVENTION

Embodiment 1

Figure 1:
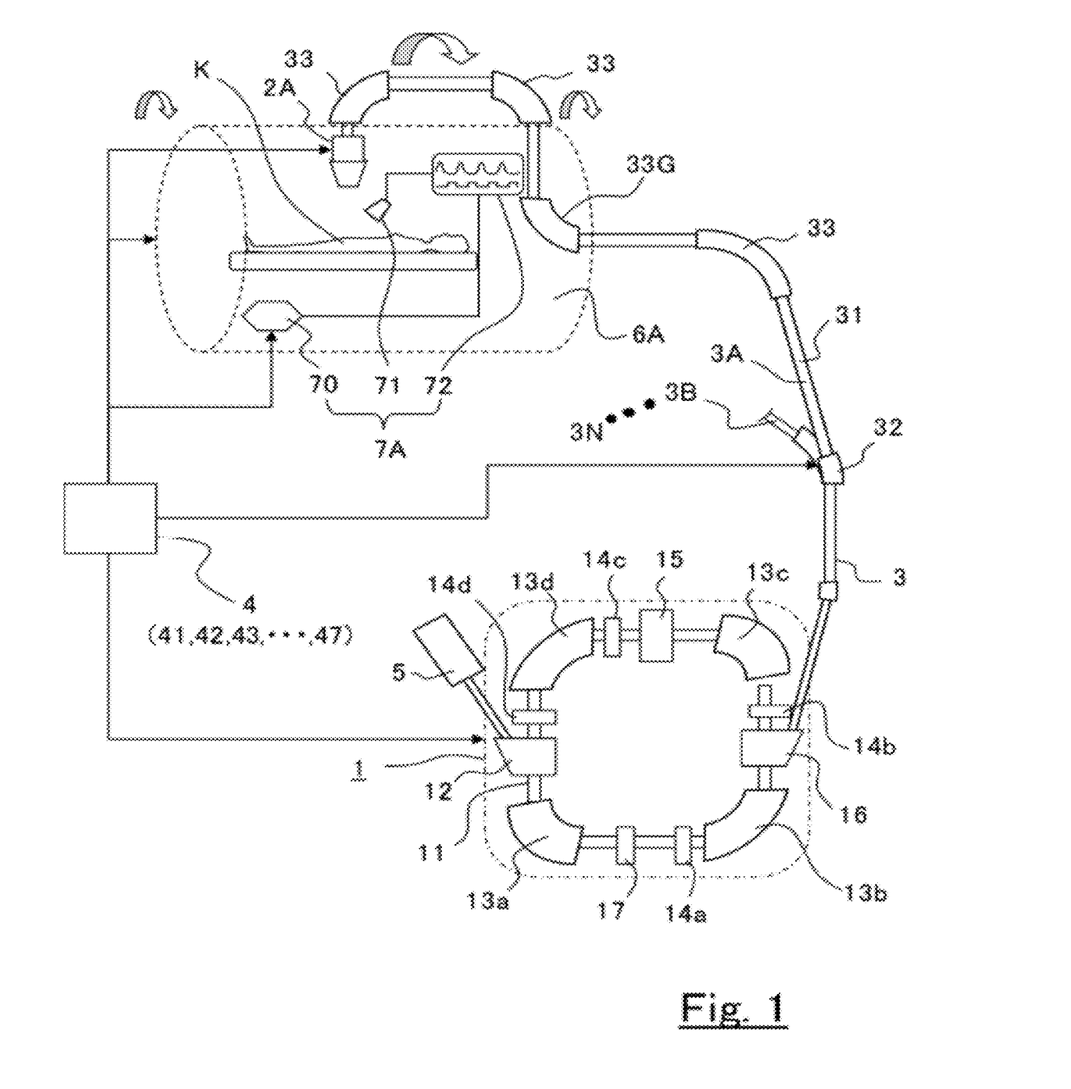
FIG. 1 is a diagram for explaining the overall configuration of a particle beam therapy system according to Embodiment 1 of the present invention.
Figure 2:
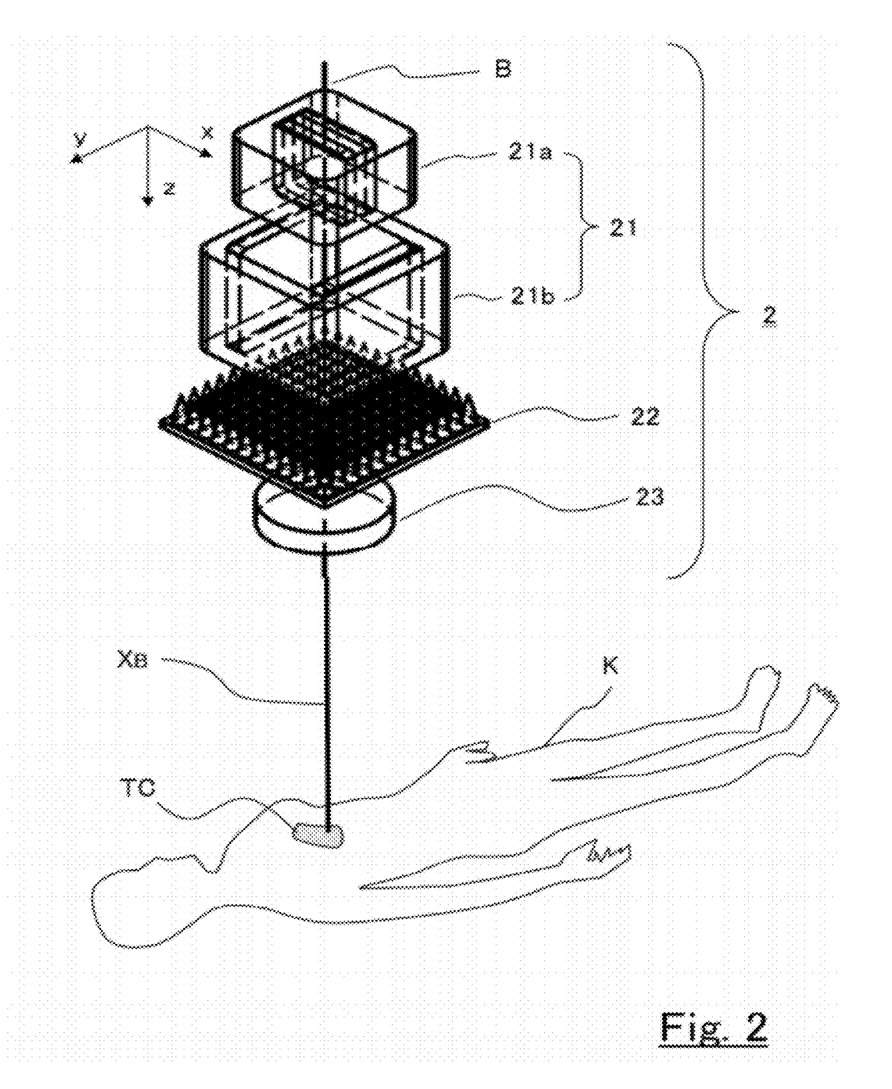
FIG. 2 is a view for explaining the configuration of an irradiation apparatus in a particle beam therapy system according to Embodiment 1 of the present invention.
Figure 3:
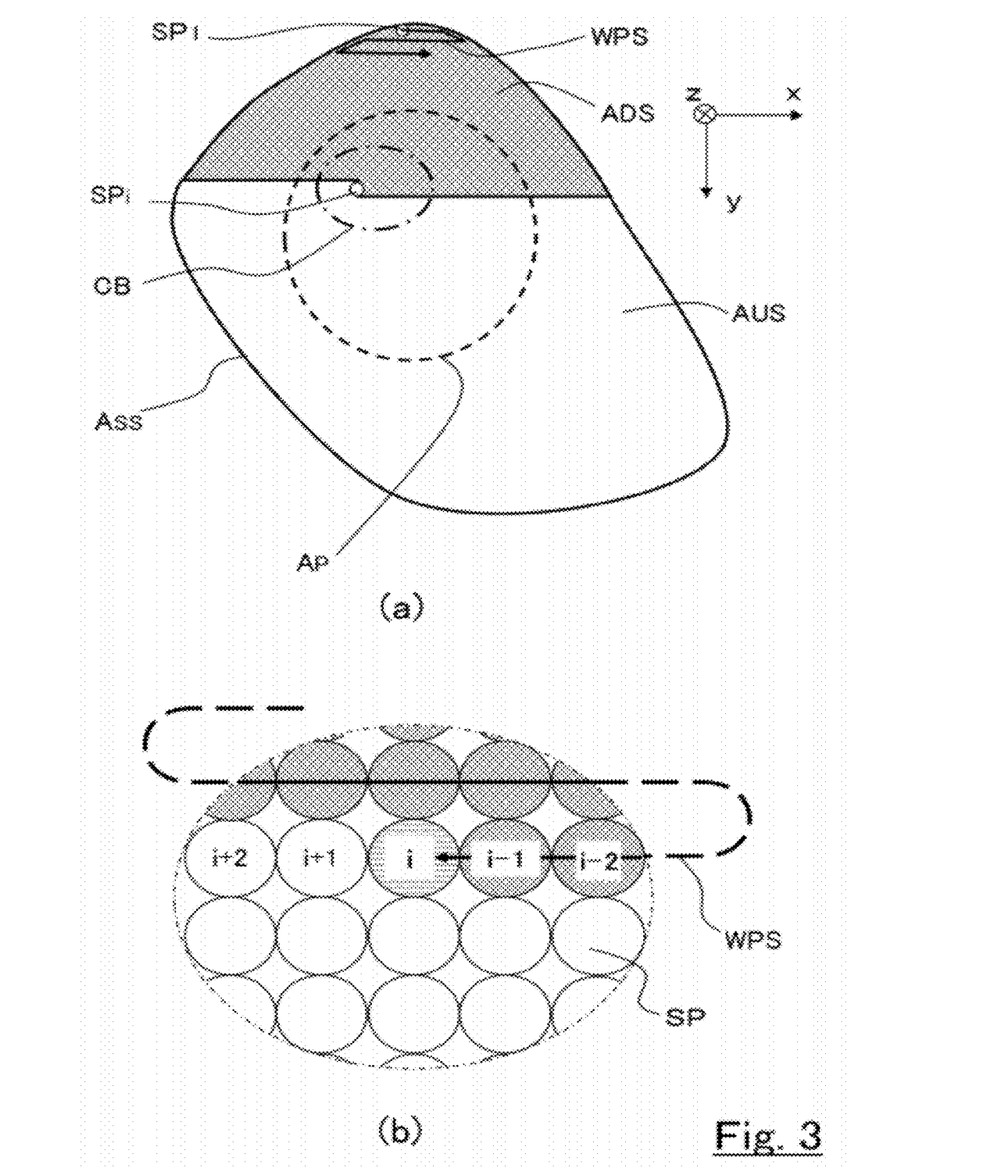
FIG. 3 is a set of views for explaining a scanning irradiation method in a particle beam therapy system according to Embodiment 1 of the present invention.
Figure 4:
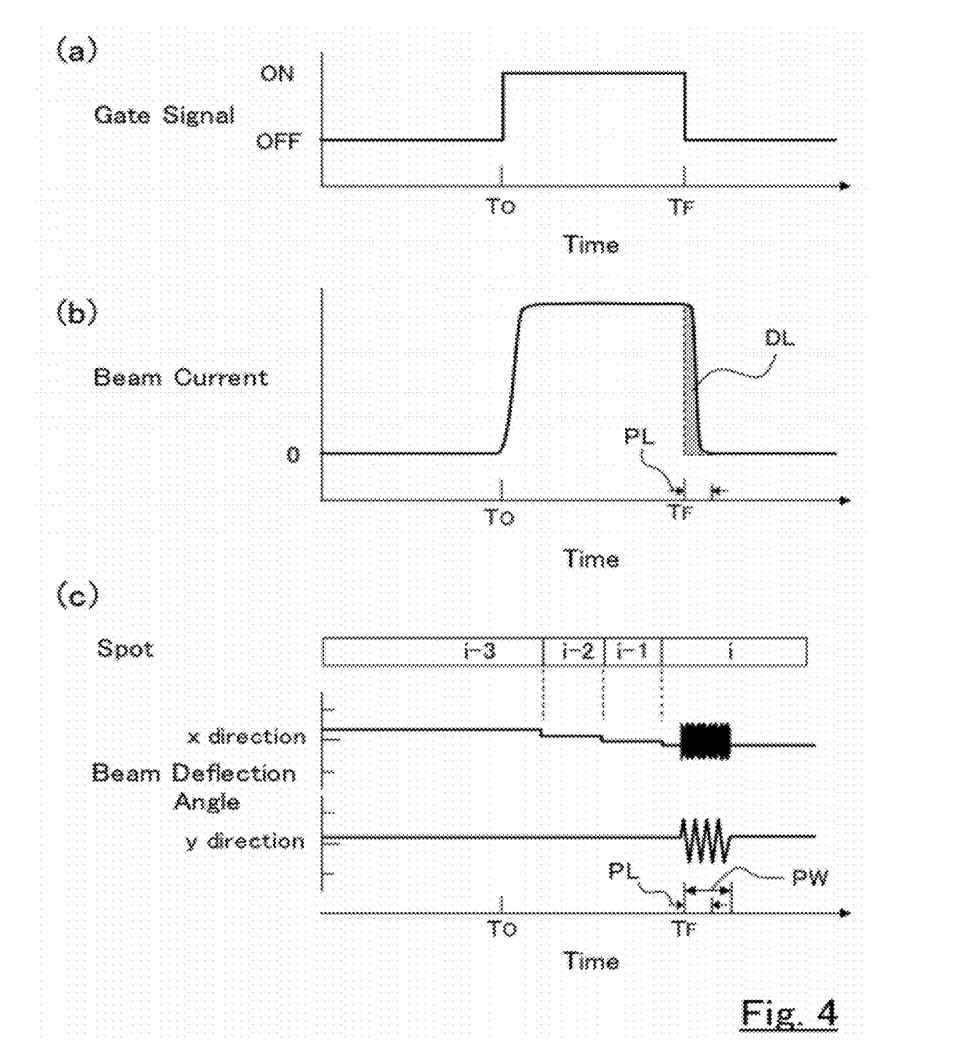
FIG. 4 is a set of waveform charts for explaining a beam control method in a particle beam therapy system according to Embodiment 1 of the present invention.

The configuration and the operation of a particle beam therapy system according to Embodiment 1 of the present invention will be explained below. Each of FIGS. 1 through 4 is a diagram, a view, or a chart for explaining the configuration and the operation of a particle beam therapy system according to Embodiment 1 of the present invention; FIG. 1 is a diagram for explaining the overall configuration of a particle beam therapy system; FIG. 2 is a view illustrating the configuration of an irradiation apparatus of a particle beam therapy system. FIG. 3 is a set of plan views of an irradiation subject for explaining a scanning irradiation method; FIG. 3(a) is a view illustrating the order of irradiation in the overall irradiation subject (the whole area); FIG. 3(b) is an enlarged view of a portion defined by the circle CB in FIG. 3(a). FIG. 4 is a set of waveform charts, for explaining a control method for a charged particle beam, that are synchronized with one another; FIG. 4(a) represents a gate signal in a respiration synchronization control; FIG. 4(b) represents a beam current that changes in synchronization with the gate signal; FIG. 4(c) represents irradiation subject spots and the respective beam deflection angles, in the x direction and the y direction, that are adjusted by a scanning electromagnet for irradiating a beam onto the spots.

It is a feature of a particle beam therapy system according to Embodiment 1 of the present invention that in the case where while irradiation onto a given spot is performed through a scanning irradiation method, there is made control of stopping a beam, based on a respiratory phase, diluting scanning is performed in such a way that a beam is swung within a predetermined range. However, before the detailed explanation for the beam control, there will be described with reference to FIG. 1 the schematic configuration of a particle beam therapy system. In FIG. 1, a particle beam therapy system is provided with a circular accelerator (just referred to as an accelerator, hereinafter) 1, which is a synchrotron as a supply source of a charged particle beam; an irradiation system equipped with irradiation apparatuses 2 provided in respective treatment rooms 6; a transport system 3 that connects the accelerator 1 with each treatment room 6 and transports a charged particle beam from the accelerator to the irradiation apparatus 2 in each treatment room 6; and a control system 4 that controls these systems. Next, the configurations will be explained.

<Accelerator>

The accelerator 1 is provided with a vacuum duct 11 that serves as an orbit path through which a charged particle beam circulates; an injector 12 for injecting a charged particle beam, supplied from a prestage accelerator 5, into the vacuum duct 11; deflection electromagnets 13a, 13b, 13c, and 13d (collectively referred to as 13) for deflecting the orbits of charged particles so that the charged particles form a charged particle beam that circulates along a circulation orbit in the vacuum duct 11; convergence electromagnets 14a, 14b, 14c, and 14d (collectively referred to as 14) for converging a charged particle beam formed on the circulation orbit not to diverge; a high-frequency wave acceleration cavity 15 that applies a high-frequency voltage, synchronized with circulating charged particles, to the circulating charged particles so as to accelerate the charged particles; an emission apparatus 16 for extracting from the accelerator 1a charged particle beam accelerated in the accelerator 1 and emitting the extracted charged particle beam into the transport system 3; and a six-pole electromagnet 17 that excites resonance in the circulation orbit of a charged particle beam in order to make the emission apparatus 16 emit the charged particle beam.

There are provided unillustrated apparatuses for controlling the respective units; for example, in the deflection electromagnet 13, there is provided a deflection electromagnet control apparatus that controls the excitation current for the deflection electromagnet 13, and in the high-frequency wave acceleration cavity 15, there are provided a high-frequency wave source for supplying a high-frequency voltage to the high-frequency wave acceleration cavity 15 and a high-frequency wave control apparatus for controlling the high-frequency wave source; an accelerator control apparatus (accelerator sub-controller 41, described later), which controls the whole accelerator 1 by controlling other components such as the deflection electromagnet control apparatus, the high-frequency wave control apparatus, and convergence electromagnet 14, and the like are also provided in the control unit 4.

In FIG. 1, for the sake of simplicity, the prestage accelerator 5 is illustrated as if it is a single apparatus; however, in practice, the prestage accelerator 5 includes an ion source (ion beam generator) that generates a charged particle (ion) such as a proton or a carbon particle (heavy particle) and a linear accelerator system that performs initial acceleration of a generated charged particle. A charged particle injected from the prestage accelerator 5 to the accelerator 1 is accelerated in a high-frequency electric field up to 70% to 80% of the light velocity, as it is being bent by means of the magnets.

<Transport System>

A charged particle beam B accelerated by the accelerator 1 is emitted to the transport system 3, which is referred to as an HEBT (High Energy Beam Transport) system. The transport system 3 is provided with a vacuum duct 31 that serves as a transport path for the charged particle beam B; a switching electromagnet 32, which is a switching device for switching the orbits of the charged particle beam B; and a deflection electromagnet 33 that deflects a beam at a predetermined angle. The charged particle beam B that has been sufficiently energized by the accelerator 1 and travels through the vacuum duct 31 is led to the irradiation apparatus 2 provided in a designated treatment room 6; changing the transport path (a transport path 3A to a treatment room 6A, a transport path 3B to a treatment room 6B, - - -, a transport path 3N to a treatment room 6N) by the switching electromagnet 32, as may be necessary.

<Irradiation System>

The irradiation system includes an irradiation apparatus 2 that forms the charged particle beam B supplied from the transport system 3 into an irradiation field conforming to the size or the depth of a diseased site TC of a patient K as an irradiation subject and irradiates the charged particle beam B onto the diseased site; and a respiration synchronization apparatus 7. In conjunction with respiration, the on/off of irradiation onto the diseased site TC as an irradiation subject is controlled (in accordance with the phase of a respiratory signal). In view of therapy efficiency, a particle beam therapy system, in general, is provided with a plurality of treatment rooms (In FIG. 1, only the treatment room A is illustrated, and with regard to treatment rooms 6B through 6N, only the numbers thereof are marked; the treatment rooms 6A through 6N are collectively referred to as the treatment room 6) for a single accelerator. In other words, in the irradiation system described herein, the irradiation apparatus 2 and the respiration synchronization apparatus 7 are provided in each treatment room 6; for example, the irradiation system for the treatment room 6A is illustrated as the combination of an irradiation apparatus 2A and a respiration synchronization apparatus 7A. The detail of the configuration of the irradiation apparatus 2 will be explained later; the explanation for the whole particle beam therapy system will be continued.

<Respiration Synchronization Apparatus>

The respiration synchronization apparatus 7 performs part of functions of a respiration synchronization control unit that controls the ON/OFF of the emission of the particle beam B from the accelerator 1 in synchronization with the respiratory phase of the patient K. Accordingly, the respiration synchronization apparatus 7 is provided with a respiration measurement apparatus for measuring the respiratory state of the patient K; a respiration synchronization apparatus main body 70 that outputs a gate signal indicating whether or not a charged particle beam from the accelerator 1 may be emitted (the ON/OFF of the emission), based on a real respiratory waveform measured by the respiration measurement apparatus 71, and that manages the whole respiration synchronization apparatus 7; and a respiration information instruction apparatus 72 for giving the patient K, a medical technologist, and the like information items on respiration synchronization, such as a desired respiratory waveform and a real respiratory waveform, for performing respiratory induction.

<Treatment Room>

The treatment room 6 is a room where therapy is performed by practically irradiating the charged particle beam B onto the patient K; basically, each treatment room has the foregoing irradiation system. In FIG. 1, the treatment room 6A is exemplified by a rotating irradiation room (referred to also as a rotating gantry) where the entire part from the deflection electromagnet 33G to the irradiation apparatus 2A revolves around the patient K (treatment table) so that the angle of irradiation of the charged particle beam B onto the patient K can freely be set. In general, for a single accelerator 1, there are provided two or more treatment rooms such as a horizontal irradiation room in which a particle beam is horizontally irradiated from an irradiation apparatus onto a patient who is fixed on a treatment table whose angle and position can freely be set and a treatment room of the other type.

<Control System>

In many cases, as the above-mentioned control system of a particle beam therapy system including a plurality of subsystems (the accelerator 1, the transport system 3, the irradiation system for each treatment room, and the like), there is utilized a hierarchical-type control system that includes a sub-controller that is dedicated to control of each subsystem and a main controller that conducts and controls the whole system. This configuration including a main controller and a sub-controller is adopted also in the control unit 4 of a particle beam therapy system according to Embodiment 1 of the present invention. The functions of the control system are shared in such a way that operations that can be controlled by the subsystem alone are controlled by the subsystem and operations to be controlled in a collaborative manner by a plurality of systems are controlled by the main controller.

Meanwhile, in general, as the control unit 4 of the particle beam therapy system, a workstation or a computer is utilized. Accordingly, because being realized by software or the like, the functions of the main controller and the sub-controller of the control unit 4 do not necessarily fall into specific hardware. Thus, although in FIG. 1, these devices are collectively illustrated as the control unit 4, it does not mean that the control unit 4 exists as a piece of physically unified hardware. Hereinafter, for example, in the case where a controller corresponding to the sub-controller of the irradiation apparatus 2 is indicated, it is described as the sub-controller 42.

Next, the configuration of the irradiation apparatus 2 will be explained. In FIG. 2, the irradiation apparatus 2 is provided with a scanning electromagnet 21 that functions as an irradiation nozzle for irradiating a so-called pencil-shaped charged particle beam B, supplied through the transport system 3 from the accelerator 1, in an arbitrary direction on a plane that is approximately perpendicular to a beam axis $X_B$; a ridge filter 22 for enlarging the width of a Bragg peak in accordance with the thickness of the irradiation subject TC; and a range shifter 23 for changing the energy (range) of the charged particle beam B in accordance with the depth (irradiation depth) of the irradiation subject. The scanning electromagnet 21 is configured with a scanning electromagnet 21a and a scanning electromagnet 21b that are arranged along the beam axis $X_B$ and the respective deflection directions of which are different from each other (e.g., the x direction and the y direction that are perpendicular to each other) on a plane (xy) that is perpendicular to the beam axis $X_B$; the scanning electromagnet 21 deflects the incident charged particle beam B in a predetermined direction with respect to the beam axis $X_B$ so that the charged particle beam B is emitted toward a predetermined position on an xy plane in the irradiation subject TC. The ridge filter 22 is formed, for example, in such a way that a great number of cones or plates whose cross sections are triangles are arranged on a plane; assuming that an irradiation spot is divided into a great number of sub-areas, there exist beams that pass through different thicknesses from one another. For easier understanding, FIG. 1 or 2 illustrates cones that are arranged on a plane. A Bragg peak is enlarged in such a manner as described above, to have desired width of SOBP (Spread-Out Bragg Peak). That is to say, the ridge filter 22 enlarges the depth-direction width where a dose can be delivered. The range shifter 23 is a device that attenuates the energy of the incident charged particle beam B by a predetermined amount; for example, there is provided a plurality of resin plate materials having predetermined thicknesses, and by combining the plate materials (through the total thickness), the amount of attenuation can be specified.

In the case where irradiation utilizing the foregoing irradiation apparatus 2 is performed according to the scanning irradiation method, spatial dose delivery is divided in the depth (z) direction and the dose is delivered. For that purpose, in a treatment plan, the diseased site TC is divided in such a way that the divisions have respective predetermined thicknesses in the depth direction. Then, as illustrated in FIG. 3, in a planar-direction shape $A_{ss}$ of each division layer (slice SS), there are arranged irradiation areas (spots SPs) having predetermined diameters (corresponding to beam diameters) in such a way that the planar-direction shape $A_{ss}$ is covered without any empty space, and the dose of each spot SP and the irradiation path WPS are preliminarily specified.

Basically, irradiation is started from a layer (slice SS) that includes the deepest portion of the diseased site TC. At first, the energy (range: attainable depth) of the charged particle beam B to be irradiated from the irradiation apparatus is set in accordance with the depth of the deepest-portion slice $SS_1$. Because, basically, to set the energy is to adjust the velocity (kinetic energy) of the charged particle beam B emitted from the accelerator 1, the setting is performed by controlling the operation of the accelerator 1 through the sub-controller 41; however, in the case where there is required to implement the setting more finely than the energy is adjusted by the accelerator 1, the setting is implemented by utilizing the range shifter 23. The charged particle beam B, the energy of which is adjusted in such a way that the range thereof becomes a predetermined range and which is then supplied from the accelerator, passes through the transport system 3 and is supplied, as a so-called pencil beam having a diameter of several millimeters, to the irradiation apparatus 2. When passing through the scanning electromagnet 21, the charged particle beam B that has been supplied to the irradiation apparatus 2 is deflected by respective predetermined angles in the x direction (21a) and the y direction (21b) with respect to the beam axis XB, in accordance with the position of a spot SP; then, the irradiation direction is changed in such a way that the charged particle beam B heads for the spot SP. Then, the charged particle beam B that has been emitted toward the spot SP passes through the ridge filter 22, so that the Brag peak is enlarged (SOBP) in such a way as to correspond to the thickness of the slice SS. The charged particle beam B further passes through the range shifter 23, so that the range is finely adjusted; by adjusting the irradiation amount (beam current× time), the charged particle beam B of a predetermined dose can be irradiated onto a predetermined spot SP in the slice $SS_1$.

When in such a way as described above, the irradiation onto the deepest-portion layer (slice $SS_1$) is completed, irradiation onto the next slice $SS_2$ is started. At this time, the range is adjusted by the accelerator 1 and the range shifter 23 in such a way that the energy of the charged particle beam B is lowered (the range becomes shorter) by the amount of energy corresponding to the thickness of the slice SS; in accordance with the spot layout and the irradiation path WPS corresponding to the next slice $SS_2$, scanning irradiation onto the slice $SS_2$ is performed. After that, the range, the layout of the spot SP, and the irradiation path are adjusted every slice $SS_j$ in a similar manner, so that as a whole, a dose optimized for the shape of the diseased site TC is delivered.

In the irradiation control inside the slice SS in each slice SS, the particle beam therapy system according to Embodiment 1 performs control in which the element of raster scanning is adopted in the spot scanning method. In other words, when in each slice SS and in accordance with the irradiation path WPS, irradiation onto an initial spot $SP_1$ through a final spot $SP_N$ is sequentially performed while positioning is implemented, transition between the spots SPs is performed at high speed while a beam is irradiated as in the raster scanning. In general, in a single slice SS, there are allocated several hundreds of spots SPs to several hundreds of thousands of spots SPs; however, when the charged particle beam B is cut off every transition between the spots SPs, the time for cutting off the beams becomes long, whereby the therapy time becomes long. However, by means of high-speed transition between the spots SPs during continuous irradiation, it is made possible to suppress the number of cutoffs of the charged particle beam B in the slice SS so as to reduce the irradiation time, without delivering unnecessary doses onto portions other than the spots SPs.

Meanwhile, in the irradiation as described above, in the case where the irradiation subject TC moves due to respiration, there is performed respiration synchronization in which irradiation is implemented only at a predetermined respiratory phase where the position and the shape of the irradiation subject TC are stable. In this case, it is required to interrupt the beam irradiation even during irradiation inside the slice SS. For example, as illustrated in FIG. 3, there exists a case where in an irradiation area $A_{SS}$, which is the plane shape, in the xy-plane direction, of a given slice SS, irradiation has been completed in the area (an irradiated area ADS) from the spot $SP_1$ to the spot $SP_{i-1}$, and halfway through the irradiation onto the spot $SP_i$, a beam is stopped due to a respiratory phase. The biggest feature of the particle beam therapy system according to Embodiment 1 of the present invention exists in the control of beam irradiation at a time when as described above, beam irradiation is interrupted halfway in the spot SP (slice SS). Detailed explanation will be made below with reference also to the waveform chart in FIG. 4.

FIGS. 4(a) through 4(c) represent the gate signal, the beam current, and the beam deflection angle, respectively, in the foregoing situation. The ordinate in FIG. 4(a) denote the gate signal; the lower side thereof is the state where a gate OFF, which is beam cutoff, is instructed; the upper side thereof is the state where a beam ON, which is beam irradiation, is instructed. The ordinate in FIG. 4(b) denotes a beam current, which indicates the amount of a beam that is actually irradiated. FIG. 4(c) represents the irradiation subject spot and the beam deflection angle for irradiating a beam onto the irradiation subject spot. The deflection angle is represented in such a way as to be divided into two ordinates; the upper ordinate represents the deflection angle, of the charged particle beam B with respect to the beam axis $X_B$, that is adjusted by the scanning electromagnet 21a that deflects a beam in the x direction; the lower ordinate represents the deflection angle, of the charged particle beam B with respect to the beam axis $X_B$, that is adjusted by the scanning electromagnet 21b that deflects a beam in the y direction. The abscissas in FIGS. 4(a) through 4(c) denote the time axes that are synchronized with one another; $T_O$ denotes a time instant when the gate signal turns from OFF to ON so that restarting of a beam is instructed; $T_F$ denotes a time instant when the gate signal turns from ON to OFF so that cutoff of a beam is instructed.

Here, it is assumed that irradiation is being performed in a treatment room and that the respiration synchronization apparatus main body 70 is the sub-controller 47 and functions as part of the respiration synchronization control unit. When determining, based on a real respiratory waveform measured by the respiration measurement apparatus 71, that the respiratory phase of the patient K is a phase at which the displacement of the diseased site TC becomes large, the sub-controller 47 that functions as the respiration synchronization control unit outputs a gate signal for turning off the irradiation. The control unit 4 (that functions as the respiration synchronization apparatus in collaboration with the sub-controller 47) that received the gate signal instructs the sub-controller 41 for the accelerator 1 to turn off (cut off a beam) the emission of the charged particle beam B from the accelerator in synchronization with the gate signal. Then, the charged particle beam B, which is emitted from the accelerator 1 to the irradiation apparatus 2, is cut off.

However, as represented in FIGS. 4(a) and 4(b), even when the gate signal turns to OFF, the beam current does not immediately becomes "0" at the switchover time point $T_F$ and remains for a period PL. The integration amount DL of the beam current in the period PL is irradiated, as a leakage dose, from the irradiation apparatus 2. In this situation, if the deflection angle of the scanning electromagnet 21 is kept aimed at the spot $SP_i$, an excessive dose corresponding to the DL is irradiated onto the spot $SP_i$. However, in the case of the particle beam therapy system according to Embodiment 1, in at least a predetermined period (e.g., a period that begins from $T_F$ and is as long as can cover PL) where it is recognized that there exists an effect of a leakage dose, the operation of the irradiation apparatus 2 is switched so that diluting scanning is performed within an allowable area $A_P$, in the irradiation area $A_{ss}$ of the slice SS, that is further limited. It may be allowed that instead of the predetermined period, a sensor for observing a beam is provided and irradiation is continued until the beam is cut off. In other words, the scanning electromagnet 21 is controlled in such a way as to perform scanning for diluting a leakage dose when a beam is emitted. The allowable area $A_P$ is set in such a way as to have an area that is the same as or wider than a certain area, for example, an area that is 100 times as wide as the spot diameter, and a leakage dose is diluted within the area.

With reference to, for example, FIG. 4(c), there will be explained the operation, at and around the switchover time point $T_F$, of the scanning electromagnet 21. It is assumed that the irradiation subject at a time when the gate signal turns to ON is the spot $SP_{i-3}$, and after the gate signal has turned to ON, the irradiation subject sequentially advances to the spots $SP_{i-2}$, $SP_{i-1}$, and $SP_i$, and then the gate signal turns to OFF at the time point $T_F$ when irradiation onto the spot $SP_i$ is being performed. In the part where no beam cutoff is taken into consideration, because as represented in FIG. 3(b), the position in the y direction does not change in the spots $SP_{i-3}$ through $SP_i$, the y-direction deflection angle is basically a constant value. In contrast, because the position moves in the x direction, only the x-direction deflection angle changes as the subject spot SP changes. At this time, the speed of transition between the spots is high and hence the time required for transition between the spots is short in comparison to the dwelling time at each spot; therefore, the waveform becomes approximately step-like.

Then, at the switchover time point $T_F$, the charged particle beam B is scanned at as high speed as when a beam moves between the spots so that the leakage dose DL is diluted within the allowable area $A_P$, i.e., the charged particle beam B is scanned in such a way as to swing; therefore, during the period PW, the x-direction deflection angle and the y-direction deflection angle change largely. In FIG. 3(b) represents change in the deflection angle, assuming that as is the case with the path WPS, there is repeatedly scanned a single-stroke-drawing path that changes in the y direction while folding in the x direction in the approximately elliptical allowable area A. After the diluting scanning period PW ends, the scanning electromagnet 21 is controlled in such a way as to adjust a deflection angle corresponding to the spot $SP_i$ where beam irradiation has been interrupted. Therefore, when the respiration gate becomes ON next time, the scanning electromagnet 21 is controlled in such a way as to adjust a deflection angle accurately corresponding to the spot $SP_i$ and the irradiation is continued, so that the irradiation period for the spot $SP_i$ can appropriately be adjusted while the gate signal is ON.

In other words, in the scanning irradiation, there may exist a case where beam cutoff operation intervenes in the period in which irradiation onto a given spot is performed according to the gate signal, or a case where at the final time point for each slice, beam cutoff operation intervenes immediately after irradiation onto the final spot SP ends. However, even though the beam cutoff operation intervenes, scanning is performed in such a way that leakage irradiation at a time of cutoff disperses within the allowable area $A_P$ that has a predetermined area; thus, the dose is diluted and hence the dose does not concentrate in a specific portion, whereby there can be performed dose delivery conforming to a treatment plan.

In addition, in FIG. 4(c), there are represented four irradiation spots within a single gate-ON signal; however, for the sake of explanation, the number of represented spots is limited. In fact, irradiation onto further more spots is performed and there is also performed irradiation onto a y-direction different spot in FIG. 3; thus, at that time, the deflection angle also changes in accordance with the y-direction position.

It is not necessarily required to set the allowable area $A_P$ to be smaller than the irradiation area $A_{ss}$ of a slice; the allowable area $A_P$ may be as large as the irradiation area $A_{ss}$. However, when the gate signal becomes OFF, it is suggested that an organ, which is the irradiation subject TC, is likely to move. Accordingly, in order to prevent an excessive dose from being delivered to normal tissues around the irradiation subject TC, it is desirable to set the allowable area $A_P$ inside the irradiation area $A_{ss}$, taking a margin into consideration. Furthermore, when the displacement (in direction and distance) of the organ caused by respiration is known, it may be allowed to appropriately change the amount of the margin or the allowable area $A_P$ itself in accordance with the displacement. It is not required that the allowable area $A_P$ includes the spot SP onto which irradiation is performed at the time point $T_F$; it may be allowed that the allowable area $A_P$ and the spot SP are set separately from each other. It may be allowed that the allowable area $A_P$ is appropriately changed in accordance with the timing of performing switching to the diluting scanning or the subject spot. It is not required that the path of diluting scanning in the allowable area $A_P$ is the same as the path of the spot scanning; the diluting scanning may be performed through a path having another shape such as a spiral shape. In the case of diluting scanning, scanning may be performed in such a way as to be swung as the so-called Wobbler irradiation; however, unlike the Wobbler irradiation, it is not required to homogenize the dose distribution within an irradiation range; it is only necessary to prevent the dose from converging onto a specific portion.

This kind of irradiation can be realized by controlling the scanning electromagnet 21 within a deflection angle range for forming an ordinary irradiation field; therefore, it is not required to change the specification of the scanning electromagnet or to provide an additional deflection electromagnet. Furthermore, because the operation amount (the opening degree of the deflection angle) of the scanning electromagnet at a time when diluting scanning is performed is basically within the operation amount at a time when ordinary irradiation is performed, the diluting scanning neither causes a hysteresis, which is different from the ordinary hysteresis, in the scanning electromagnet nor deteriorates the accuracy of the scanning. Moreover, in the control unit 4, it is not required to utilize extra hardware, as long as there is added a sequence program for switching the operation over to diluting scanning. Although it may be required to enhance the storage capacity as data on the operation amount for the diluting scanning is added, it is only necessary to provide a predetermined amount of storage capacity in order to deal with this; thus, measures may be taken just to the extent of so-called skill-up of an ordinary computer.

In addition, the foregoing diluting scanning is not limited to be performed only when a beam is cut off. For example, in the case where at the time point $T_O$ when a beam irradiation is resumed, there exists a period where a beam current is unstable and the effect of the dose during the period is as large as can be prevented by dilution, the diluting scanning may be utilized in such a way as to cover the period. In this case, it is required that when the dose is calculated, the period where the diluting scanning is performed is subtracted from the gate-ON time.

As described above, a particle beam therapy system according to Embodiment 1 is provided with an accelerator 1 that accelerates and emits a charged particle beam (particle beam) B, a scanning electromagnet 21 that is a set of two electromagnets 21a and 21b whose scanning directions are different from each other, and functions as an irradiation nozzle for irradiating in a predetermined direction the particle beam B emitted from the accelerator 1, an irradiation control unit 42 (or control unit 4 provided with it) that controls the operation of an irradiation nozzle 21 in such a way that while positioning is performed, the particle beam B of a predetermined dose is sequentially irradiated onto each of two or more spots set, according to a treatment plan, within a planar-direction (shape) $A_{ss}$ of an irradiation subject TC, and a control unit 4 (and a sub-controller 47) that functions as a respiration synchronization control unit for controlling the ON/OFF of emission of the particle beam B from the accelerator 1 in synchronization with a respiratory phase of a patient K. The irradiation control unit 42 is configured in such a way as to make the irradiation nozzle 21 scan the particle beam B, so as to dilute the leakage dose DL, onto the predetermined area $A_P$ set in the planar-direction (shape) $A_{SS}$ in an irradiation subject, in a predetermined period PW after the time point $T_F$ when the emission of the particle beam B is switched from ON to OFF in synchronization with the respiratory phase or in a period from $T_F$ to a time point when the particle beam B is cut off; therefore, even when a beam is cut off through respiration synchronization during irradiation onto a given spot SP or a given slice SS, the leakage dose DL, which is produced during beam cutoff, is diffused within the allowable area $A_P$ having a predetermined area in the irradiation subject $A_{SS}$. As a result, no unnecessary dose is delivered to a specific spot SP, so that a dose can be delivered as per the treatment plan. Because the Wobbler scanning in the allowable area $A_P$ can be performed within the operation amount of the scanning electromagnet 21; therefore, it is not required to add an extra apparatus or to change the specification of a scanning electromagnet for ordinary scanning irradiation. In addition, the orbit of a particle beam is not bent toward the outside of the irradiation area; thus, no leakage dose is irradiated onto peripheral tissues of the irradiation area.

In particular, when the allowable area $A_P$ is set in an area obtained by adding a predetermined margin to the irradiation area $A_{SS}$, taking into account the displacement of an organ, which is the irradiation subject TC, i.e., set from an area of the irradiation subject TC in a planar-direction (shape) $A_{SS}$ to an inside of predetermined width, no leakage dose is delivered to normal tissues.

Alternatively, when the allowable area $A_P$ is set based on the displacement (direction and travel amount) of the irradiation subject TC caused by change of the respiratory phase, no leakage dose is delivered to normal tissues that travel due to respiration.

When the allowable area $A_P$ is set in accordance with the position of the spot SP, which has been an irradiation subject at the switchover time point $T_F$, there can be set a diluting scanning area in accordance with the spot, whereby there can smoothly be performed switching from the cutting-off (diluting scanning) mode to the normal (scanning irradiation) mode.

In addition, when the predetermined period PW during which diluting scanning is performed is determined based on a period $P_L$ from the time point $T_F$ when the accelerator 1 is switched from ON to OFF to a time point when the emission of the particle beam B is stopped, the leakage dose DL can securely be dispersed and diluted in the allowable area $A_P$.

Embodiment 2

In Embodiment 1, the irradiation nozzle 21 performs diluting scanning onto the predetermined area $A_P$ set in the planar-direction $A_{SS}$ in an irradiation subject, in the predetermined period PW after the time point $T_F$ when the emission of the particle beam is switched from ON to OFF in synchronization with the respiratory phase, so that the leakage dose DL is dispersed and diluted in the predetermined area $A_P$; however, in the scanning irradiation, the operation of switching the emission of a particle beam from ON to OFF is not limited to be performed in synchronization with the respiratory phase. For example, also at a completion time, of irradiation onto a final spot, that is a last time point for scanning irradiation onto each slice SS, the emission of the particle beam is switched from ON to OFF.

In a particle beam therapy system according to Embodiment 2 of the present invention, a leakage dose DL, arising in the case where the emission of the beam B is switched from ON to OFF at the completion time of irradiation onto the last spot of each slice SS, is dispersed and diluted in the allowable area $A_P$ through scanning. In the scanning irradiation, the arrangement of spots SPs and the irradiation path WPS for each slice SS and the dose for each spot SP are preliminarily determined by a treatment plan. Then, as per a schedule determined by a treatment plan, irradiation onto the initial spot $SP_1$ of a slice SS is performed; when the irradiation dose for the initial spot $SP_1$ reaches a dose determined by the treatment plan, scanning moves to the next spot $SP_2$; similarly, when the irradiation dose reaches a dose determined by the treatment plan, scanning moves further to the next spot $SP_3$. In such a way as described above, irradiation onto the final spot $SP_N$ of the slice SS is performed; when the irradiation dose for the final spot $SP_N$ reaches an irradiation dose determined by the treatment plan, instruction for cutting off the beam B is issued.

Also at this time, as explained with reference to FIG. 4, the beam cutoff is not completely performed at the time point $T_F$ when the beam cutoff is instructed and hence a beam current remains for a period PL; thus, a leakage dose DL corresponding to the integration amount of the beam current is delivered to the final spot $SP_N$. In Embodiment 2, the leakage dose DL at a time when irradiation onto the final spot $SP_N$ of each slice ends is dispersed and diluted in the allowable area $A_P$ through diluting scanning, as is the case with Embodiment 1. As a result, no unnecessary dose is delivered to a specific spot, so that a dose can be delivered as per the treatment plan.

As described above, a particle beam therapy system according to Embodiment 2 is provided with an accelerator 1 that accelerates and emits a charged particle beam (particle beam) B; a scanning electromagnet 21 that is a set of two electromagnets 21a and 21b whose scanning directions are different from each other, and functions as an irradiation nozzle for irradiating in a predetermined direction the particle beam B emitted from the accelerator 1; an irradiation control unit 42 (or control unit 4 provided with it) that controls the operation of an irradiation nozzle 21 in such a way that with regard to a plurality of slices SSs obtained by dividing the irradiation subject TC in the depth direction according to a treatment plan, the particle beam B of a predetermined dose is sequentially irradiated onto each of two or more spots SPs set within a planar-direction (shape) $A_{ss}$ in each slice SS, while positioning is performed; and a control unit 4 that turns off the emission of a particle beam from the accelerator 1 when irradiation onto the final spot $SP_N$ of each of the plurality of slices SSs is completed. When irradiation onto the final spot $SP_N$ of the slice SS ends, the irradiation control unit 42 makes the irradiation nozzle 21 scan the particle beam B onto a predetermined area $A_P$ set in the planar-direction (shape) $A_{SS}$ in an irradiation subject, so as to dilute a leakage dose DL, in a predetermined period PW after the time point $T_F$ when the emission of the particle beam B is switched from ON to OFF or in a period from $T_F$ to a time point when the particle beam B is cut off; therefore, when a beam is cut off after irradiation onto the final spot $SP_N$ of a given slice SS ends, the leakage dose DL, arising during beam cutoff, is diffused within the allowable area $A_P$ having a predetermined area in the irradiation subject $A_{SS}$. As a result, no unnecessary dose is delivered to the final spot $SP_N$ of each slice SS, so that a dose can be delivered as per the treatment plan. Because the Wobbler scanning in the allowable area $A_P$ can be performed within the operation amount of the scanning electromagnet 21; therefore, it is not required to add an extra apparatus or to change the specification of a scanning electromagnet for ordinary scanning irradiation. In addition, the orbit of a particle beam is not bent toward the outside of the irradiation area; thus, no leakage dose is irradiated onto peripheral tissues of the irradiation area.

The present invention is not limited to a case where a beam is cut off in such a manner as described in each of Embodiments 1 and 2; the present invention is to perform diluting scanning so as to disperse and dilute a leakage dose produced when a beam is cut off during scanning irradiation; it goes without saying that the present invention can be applied to cases where a beam is cut off for other reasons. The following are among the other reasons: a case where a beam is cut off because a safety interlock operates due to the apparatus abnormality such as fluctuation in the intensity of the beam from an accelerator or fluctuation in the position of the beam, or due to a sudden change in patient condition; and a case where even in a single and the same slice, a beam is temporarily cut off based on a treatment plan.

In other words, a particle beam therapy system according to any one of Embodiments 1 and 2 is provided with an accelerator 1 that accelerates and emits a charged particle beam (particle beam) B; a scanning electromagnet 21 that is a set of two electromagnets 21a and 21b whose scanning directions are different from each other, and functions as an irradiation nozzle for irradiating in a predetermined direction the particle beam B emitted from the accelerator 1; an irradiation control unit 42 (or control unit 4 provided with it) that controls the operation of an irradiation nozzle 21 in such a way that while positioning is performed, the particle beam B of a predetermined dose is sequentially irradiated onto each of two or more spots set in each of plurality of slices SSs obtained by dividing an irradiation subject TC in the depth direction or within a planar-direction (shape) $A_{ss}$ of the irradiation subject TC; and a control unit 4 that turns off the emission of a particle beam from the accelerator 1. The irradiation control unit 42 is configured in such a way as to make the irradiation nozzle 21 scan the particle beam B onto a predetermined area $A_P$ set in the planar-direction (shape) $A_{SS}$ in an irradiation subject, so as to dilute a leakage dose DL, in a predetermined period PW after the time point $T_F$ when the emission of the particle beam B is switched from ON to OFF or in a period from $T_F$ to a time point when the particle beam B is cut off; therefore, even when a beam is cut off through respiration synchronization during scanning irradiation, the leakage dose DL, arising during beam cutoff, is diffused within the allowable area $A_P$ having a predetermined area in the irradiation subject $A_{SS}$. As a result, no unnecessary dose is delivered to a specific spot SP, so that a dose can be delivered as per the treatment plan. Because the Wobbler scanning in the allowable area $A_P$ can be performed within the operation amount of the scanning electromagnet 21; therefore, it is not required to add an extra apparatus or to change the specification of a scanning electromagnet for ordinary scanning irradiation. In addition, the orbit of a particle beam is not bent toward the outside of the irradiation area; thus, no leakage dose is irradiated onto peripheral tissues of the irradiation area.

Embodiment 3

In a particle beam therapy system according to Embodiment 1, a so-called leakage dose, which arises at a beam cut off timing during respiration synchronization irradiation, is scanned within a predetermined area, so that the leakage dose is diluted and the effect thereof is reduced. In contrast, in a particle beam therapy system according to Embodiment 3, there is provided a dose monitor, and even when a beam is stopped, dose counting by the dose monitor is not stopped but continued; based on whether or not the dose counted for each spot has reached a predetermined value, irradiation moves to the next spot. In other words, based on not whether or not a charged particle beam is cut off or the time of irradiation onto the spot but the measurement value of a dose that has been irradiated onto a designated spot, scanning irradiation is advanced.

Figure 5:
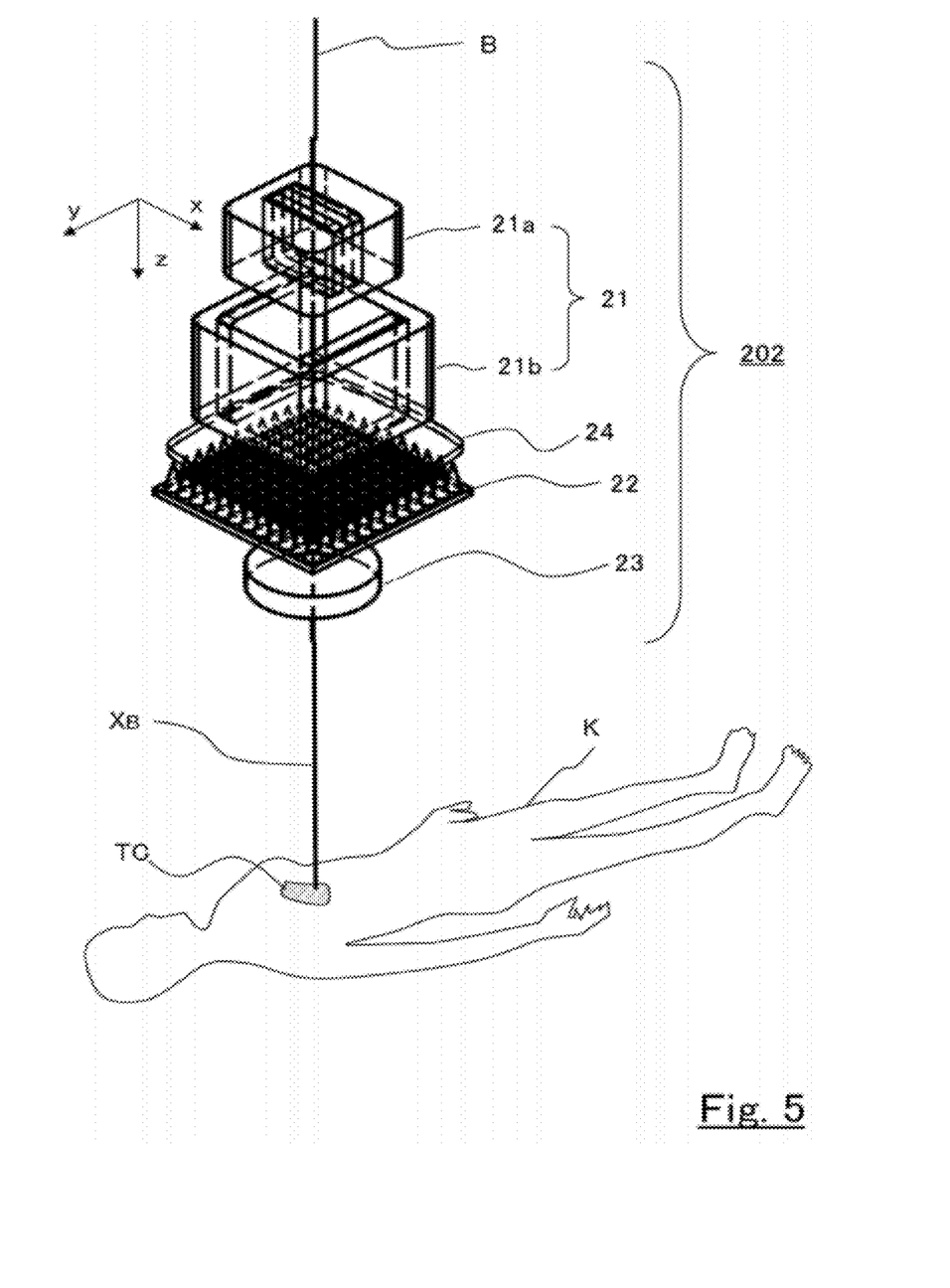
FIG. 5 is a view for explaining the configuration of an irradiation apparatus in a particle beam therapy system according to Embodiment 3 of the present invention.
Figure 6:
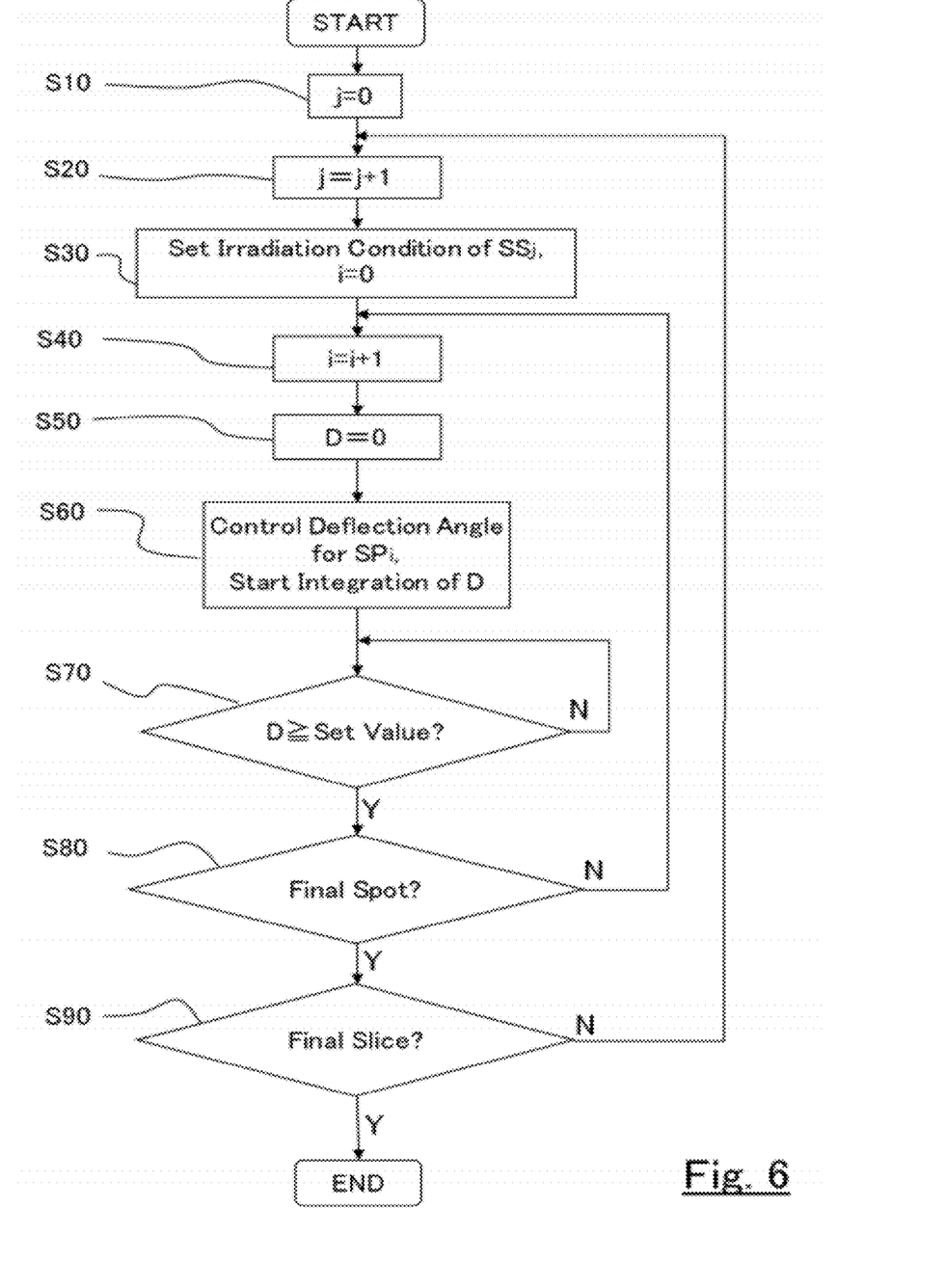
FIG. 6 is a flowchart for explaining an irradiation control method in a particle beam therapy system according to Embodiment 3 of the present invention.

FIGS. 5 and 6 are a view and a flowchart for explaining the configuration and the operation, respectively, of a particle beam therapy system according to Embodiment 3 of the present invention; FIG. 5 is a view illustrating the configuration of an irradiation apparatus in a particle beam therapy system; FIG. 6 is a flowchart for explaining the irradiation method in a particle beam therapy system. The hardware of a particle beam therapy system according to Embodiment 3 is the same as that of a particle beam therapy system according to Embodiment 1 except for a dose monitor 24 that is provided in an irradiation apparatus 202, as illustrated in FIG. 5, for measuring a beam dose. The particle beam therapy system according to Embodiment 3 is characterized in that unlike a particle beam therapy system according to Embodiment 1, there is performed no extra operation control such as switching over to diluting scanning at a time of beam cutoff, and, as represented in FIG. 6, irradiation onto each spot is controlled based on the integration value of doses measured by the dose monitor 24.

With reference to the flowchart in FIG. 6, the irradiation method will be explained.

When irradiation is started, the number of a slice SS to be scanned at first is set (the steps S10 and S20). Next, there are set an irradiation area $A_{SS}$ and the positions of spots SPs in accordance with the slice SS, an irradiation path and irradiation doses, and other irradiation conditions (the step S30). Then, when the scanning electromagnet 21 controls the deflection angle for each subject spot SP, integration of the doses at the spot SP is started based on the measurement value of the dose monitor 24 (the steps S40 through S60). In the case where an integration value D of the measured dose has not reached a setting value ("N" in the step S70), there is maintained the state where the deflection angle is controlled to aim at the spot SP. In contrast, in the case where the integration value D of the measured dose has reached the setting value ("Y" in the step S70) and the spot SS is not the final spot ("N" in the step S80), the next spot SP is irradiated (the step S40). In the case where the spot SP is the final spot ("Y" in the step S80), it is determined whether or not the present slice is the final slice; in the case where the present slice is not the final slice ("N" in the step S90), the present slice is followed by the next slice SS (the step S20), where the same operation is repeated. In the case where the present slice is the final slice SS ("Y" in the step S90), the irradiation is ended.

In these flows, even when beam cutoff operation is activated by a gate signal, the operation of the scanning electromagnet is not changed in particular, and control for the spot SP specified by the presently set deflection angle is performed based only on the integration value of the real measurement values of the doses of the supplied charged particle beam B. Assuming that 5-second-period respiration makes an organ move by 30 mm, the organ moves 6 μm in 1 msec; therefore, even if it takes 1 msec for cutting off a beam, the effect of dose nonuniformity caused by the movement of the organ is small. Accordingly, even if a leakage dose is produced when a beam is cut off, or the dose becomes unstable when beam irradiation is resumed, irradiation can be performed in such a way that the dose to be delivered to each spot becomes equal to a setting value determined by a treatment plan. In addition, in the case where the time for cutting off a beam is longer than a predetermined time, there may be taken safety measures such as activating an interlock to stop irradiation.

DESCRIPTION OF REFERENCE NUMERALS

1: accelerator
2: irradiation apparatus
3: transport system
4: control unit
5: prestage accelerator
6: treatment room
7: respiration synchronization apparatus
21: scanning electromagnet (21a: x-direction (upstream) scanning electromagnet, 21b: y-direction (downstream) scanning electromagnet)
22: ridge filter
23: range shifter
24: dose monitor
42: irradiation apparatus sub-controller (irradiation control unit)
47: respiration synchronization apparatus sub-controller (respiration synchronization control unit)
ADS: irradiated area
$A_p$: diluting scanning allowable area
$A_{SS}$: inner-slice irradiation area (planar direction in irradiation subject)
AUS: unirradiated area
B: charged particle beam (particle beam)
DL: leakage dose
K: patient
PL: leakage irradiation period
PW: diluting scanning period
SP: spot
SS: slice
TC: diseased site (irradiation subject)
$T_F$: beam switchover time point (when a beam is cut off)
$T_O$: beam switchover time point (when beam irradiation is resumed)
WPS: scanning path
$X_B$: beam axis of particle beam Three-digit numbers each denote variant examples in Embodiments.

The invention claimed is:
1. A particle beam therapy system comprising:
an accelerator that accelerates and emits a particle beam;
an irradiation nozzle that has two electromagnets whose scanning directions are different from each other and that irradiates in a predetermined direction a particle beam emitted from the accelerator;
an irradiation control unit that controls operation of the irradiation nozzle in such a way that a particle beam of a predetermined dose is sequentially irradiated onto each of a plurality of spots set in a planar direction in an irradiation subject; and
a control unit that on/off-controls emission of a particle beam from the accelerator,
wherein the irradiation control unit makes the irradiation nozzle scan the particle beam onto a predetermined area set in the planar-direction in the irradiation subject, so as to dilute a dose, in a predetermined period after a time point when emission of the particle beam is switched from ON to OFF, or in a period from the time point when emission of the particle beam is switched from ON to OFF to a time point when the particle beam is cut off.

2. The particle beam therapy system according to claim 1, wherein the control unit on/off-controls emission of a particle beam from the accelerator in synchronization with a respiratory phase of a patient.

3. The particle beam therapy system according to claim 1, wherein the plurality of spots is set in planar direction in each of a plurality of slices obtained by dividing the irradiation subject in the depth direction; and the control unit performs control in such a way as to turn off emission of a particle beam from the accelerator when irradiation onto a final spot of each of the plurality of slices is completed.

4. The particle beam therapy system according to claim 2, wherein the plurality of spots is set in planar direction in each of a plurality of slices obtained by dividing the irradiation subject in the depth direction; and the control unit performs control in such a way as to turn off emission of a particle beam from the accelerator when irradiation onto a final spot of each of the plurality of slices is completed.

5. The particle beam therapy system according to claim 1, wherein the predetermined area is set from a contour of the irradiation subject in a planar-direction to an inside of predetermined width.

6. The particle beam therapy system according to claim 2, wherein the predetermined area is set from a contour of the irradiation subject in a planar-direction to an inside of predetermined width.

7. The particle beam therapy system according to claim 3, wherein the predetermined area is set from a contour of the irradiation subject in a planar-direction to an inside of predetermined width.

8. The particle beam therapy system according to claim 4, wherein the predetermined area is set from a contour of the irradiation subject in a planar-direction to an inside of predetermined width.

9. The particle beam therapy system according to claim 2, wherein the predetermined area is set based on displacement of the irradiation subject caused by change of the respiratory phase.

10. The particle beam therapy system according to claim 4, wherein the predetermined area is set based on displacement of the irradiation subject caused by change of the respiratory phase.

11. The particle beam therapy system according to claim 1, wherein the predetermined area is set in accordance with the position of a spot that has been an irradiation subject at the time point when emission of the particle beam is switched from ON to OFF.

12. The particle beam therapy system according to claim 2, wherein the predetermined area is set in accordance with the position of a spot that has been an irradiation subject at the time point when emission of the particle beam is switched from ON to OFF.

13. The particle beam therapy system according to claim 3, wherein the predetermined area is set in accordance with the position of a spot that has been an irradiation subject at the time point when emission of the particle beam is switched from ON to OFF.

14. The particle beam therapy system according to claim 1, wherein the predetermined period is determined based on a period from a time point when the accelerator is switched from ON to OFF to a time point when emission of the particle beam is stopped.

15. The particle beam therapy system according to claim 2, wherein the predetermined period is determined based on a period from a time point when the accelerator is switched from ON to OFF to a time point when emission of the particle beam is stopped.

16. The particle beam therapy system according to claim 3, wherein the predetermined period is determined based on a period from a time point when the accelerator is switched from ON to OFF to a time point when emission of the particle beam is stopped.

17. The particle beam therapy system according to claim 5, wherein the predetermined period is determined based on a period from a time point when the accelerator is switched from ON to OFF to a time point when emission of the particle beam is stopped.

18. The particle beam therapy system according to claim 9, wherein the predetermined period is determined based on a period from a time point when the accelerator is switched from ON to OFF to a time point when emission of the particle beam is stopped.

19. The particle beam therapy system according to claim 11, wherein the predetermined period is determined based on a period from a time point when the accelerator is switched from ON to OFF to a time point when emission of the particle beam is stopped.

* * * * *